United States Patent [19]

Düsing

[11] Patent Number: 5,609,445
[45] Date of Patent: Mar. 11, 1997

[54] STRAIGHT MOTORIZED HANDPIECE, IN PARTICULAR FOR MEDICAL PURPOSES, PREFERABLY FOR A MEDICAL OR DENTAL LABORATORY

[75] Inventor: Josef Düsing, Leutkirch, Germany

[73] Assignee: Kaltenbach & Voigt GmbH & Co., Biberach, Germany

[21] Appl. No.: 389,957

[22] Filed: Feb. 17, 1995

[30] Foreign Application Priority Data

Mar. 2, 1994 [DE] Germany .......................... 44 06 855.7

[51] Int. Cl.$^6$ ................ A61C 1/05; A61C 1/08; B23B 47/04
[52] U.S. Cl. ............... 408/124; 384/477; 409/231; 433/115; 433/126
[58] Field of Search ................... 408/124, 125; 433/115, 114, 126, 129; 606/167, 168, 170, 171, 180; 384/477, 479, 483; 409/231–233

[56] References Cited

U.S. PATENT DOCUMENTS

| | | | |
|---|---|---|---|
| 2,246,471 | 6/1941 | Searles | 384/477 |
| 3,418,715 | 12/1968 | Ellis | 433/126 |
| 3,758,948 | 9/1973 | Bareth | 433/115 |
| 4,231,739 | 11/1980 | Iudica | 433/126 |
| 4,245,985 | 1/1981 | Eibofner et al. | 433/126 |
| 4,249,896 | 2/1981 | Kerfoot, Jr. | 433/126 |

Primary Examiner—Steven C. Bishop
Attorney, Agent, or Firm—Scully, Scott, Murphy & Presser

[57] ABSTRACT

In a straight motorized handpiece (101), in particular for medical purposes, preferably for a medical or dental laboratory, with a clamping device (106) arranged in a sleeve-like casing (111) for the selective clamping of tools (105) which can be inserted from the front into the handpiece (101), whereby the clamping device (106) is arranged on a drive shaft (107), which is rotatably mounted in the casing (111) by means of a rearward and a forward roller bearing (113, 114), whereby for axially retaining the drive shaft (107) a first shoulder (143) is provided on the casing (111) or on attachments thereto, against which the outer ring of one of the roller bearings (113) bears, and there is arranged a releasable arresting shoulder (145) opposite to the first shoulder (143) at an axial spacing, the first shoulder (143) is arranged on the outside of the outer ring of the associated roller bearing (113) and the arresting shoulder (145) is arranged on the outside on the other roller bearing (114), the drive shaft (107) being mountable and mountable together with the roller bearings (113, 114), as a structural unit, from that side of the casing (111) on which the releasable arresting shoulder (145) is located.

12 Claims, 4 Drawing Sheets

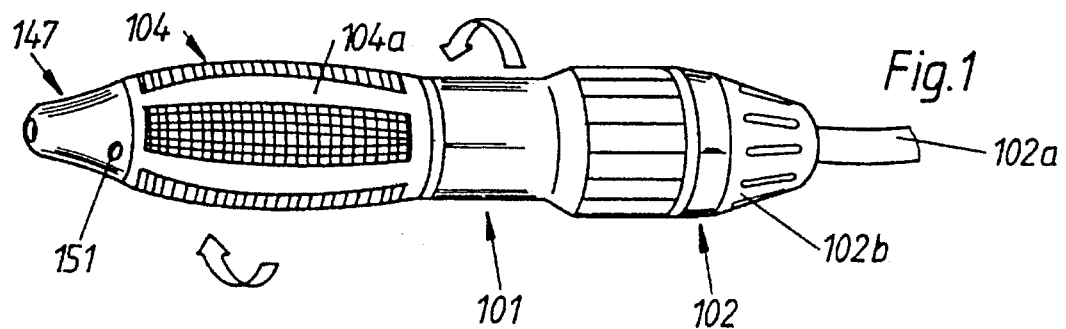
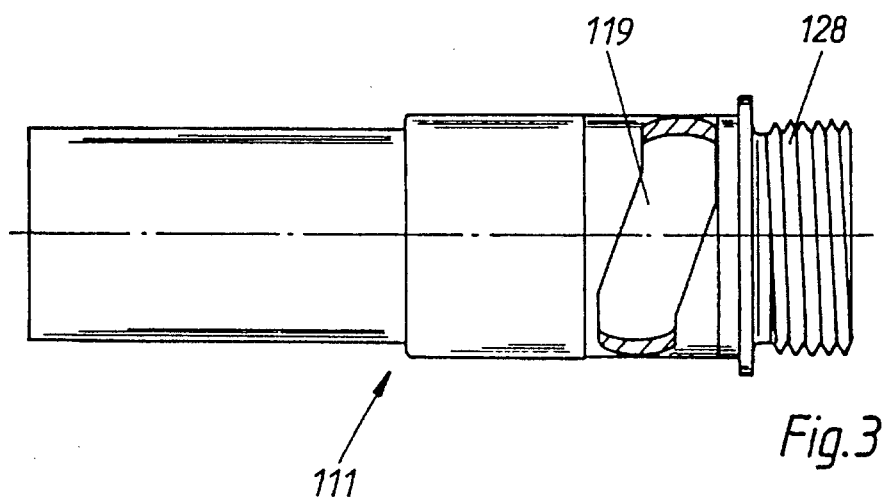

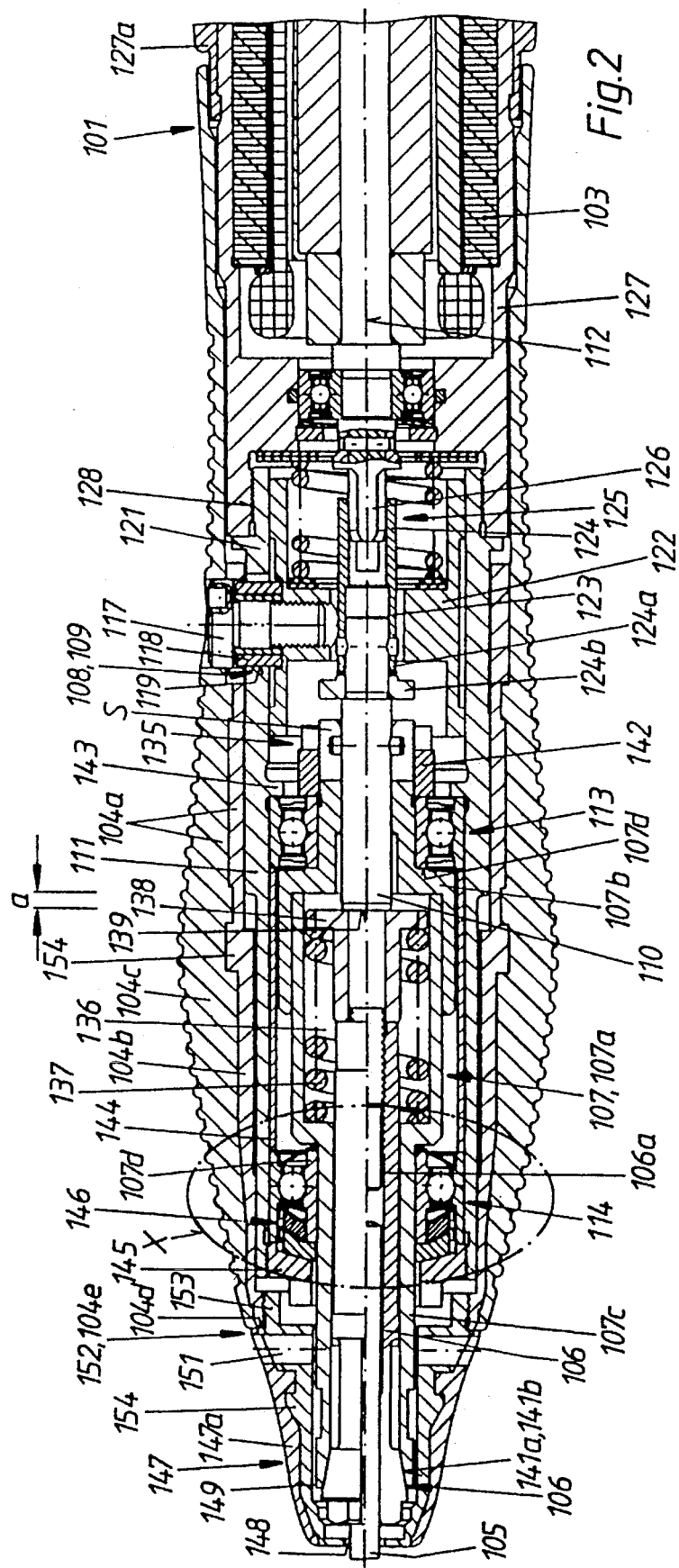

STRAIGHT MOTORIZED HANDPIECE, IN PARTICULAR FOR MEDICAL PURPOSES, PREFERABLY FOR A MEDICAL OR DENTAL LABORATORY

BACKGROUND OF THE INVENTION

1. Field of the Invention

The invention relates to a straight motorized handpiece, in particular for medical purposes, preferably for a medical or dental laboratory, with a clamping device which is arranged in a sleeve-like casing for the selective clamping of tools which can be inserted from the front into the handpiece. The clamping device is arranged on a drive shaft which is rotatably mounted in the casing by means of rearwardly and forwardly located roller bearings whereby, for axially retaining the drive shaft, a first shoulder is provided on the casing or on attachments thereto, against which there bears the outer ring of one of the roller bearings, and a releasable arresting shoulder is located opposite to the first shoulder at an axial spacing therewith.

A handpiece of the kind concerned is in particular suitable for that kind of mechanical work on natural or artificial parts of the human or animal body for which a comparatively large drive and working power is required. In the medical field such a handpiece is thus particularly suitable for work on comparatively solid parts of the body. In the dental field such a handpiece may be used for dental treatment in the oral cavity of a patient, if it is of correspondingly small construction.

A handpiece of the kind concerned is preferably suited for a medical, in particular dental laboratory, in which in particular artificial body parts or models are machined by means of rotary tools which can be clamped into the handpiece. The handpiece is suitable for the transmission of a comparatively large working power to the tool, and different tools may rapidly and readily be mounted or released and exchanged.

2. Discussion of the Prior Art

A handpiece of the kind mentioned in the introduction is marketed by the assignee under the designation K9-Handpiece Type 950 and is thus known. In the following this handpiece will be described with reference to FIG. 5.

The rod-shaped straight handpiece 1 comprises a rearward motor part 2, which is only partly illustrated, with an in particular electrical drive motor 3 mounted therein, and a forward handpiece part 4 into which, from the front, a working tool can be mounted with its shaft 5. For this purpose there serves a sleeve-like, slotted clamping chuck 6, which is part of a drive shaft 7, which is rotatably mounted coaxially in the handpiece part 4 and is connected with the drive motor 3 for rotation. The clamping chuck 6 can be opened and closed by means of a relative rotation between the motor part 2 and a grip sleeve 4a of the handpiece part 4. For this purpose an actuating mechanism 8 is integrated into the handpiece part 4, which mechanism is effective between the grip sleeve 4a and the drive shaft 7 and has a transmission 9 which converts the rotary movement of the grip sleeve 4a into an axial movement of a round draw rod 10, which extends from the rear coaxially through a bearing sleeve 7a of the drive shaft 7, is mounted therein axially displaceably in a bore and is screwed into an internal thread 6a of the clamping chuck 6 with its forward end. The grip sleeve 4a is mounted on a sleeve-like internal casing 11 to be rotatable around the longitudinal middle axis 12 of the handpiece 1 and to be longitudinally displaceable. In the internal casing 11, the drive shaft 7 is rotatably mounted by means of two roller bearings 13, 14 which have an axial spacing from one another, of which the forward roller bearing 14 bears against an internal annular shoulder 15 of the internal casing 11 with its rear side, whereby the outer ring of the roller bearing 14 is fixedly screwed against the internal ring shoulder 15 by a nut 16. The nut 16 is screwed into an internal thread at the forward end of the internal casing 11. Further, a front cap 47 is screwed into the internal thread in front of the nut 16, which cap covers the clamping chuck 6 approximately half of which projects from the internal casing 11.

The transmission 109 has a radial screw 17, which penetrates a radial hole in the grip sleeve 4a and, with a roller 18 penetrates a groove 19 in the internal casing 11 which runs obliquely in the circumferential direction, and is screwed into a pressure piece 21, which sits axially displaceably—with play for movement—in the rear end region of the hollow cylindrical internal casing 11 and has a central hole 23 in a middle inner ring 22, through which hole the drive shaft 7 projects with a plug-in connection section 24, which is connected with a drive pin 26 of the drive motor 3 by way of a plug-in coupling 125.

The motor part 2 also has an internal casing 27, in which the drive motor 3 is arranged and with which casing the motor part is screwed on to the rear end of the internal casing 11 of the handpiece part 4, at 28, whereby the grip sleeve 4a rearwardly overlaps the forward end of the motor part 2.

With this known handpiece the drive shaft 7 is, in the regions which lie behind the internal ring shoulder 15, greater in cross-section than the free internal cross-section of the internal ring shoulder 15.

After certain periods of use of the handpiece it is necessary to exchange the bearings 13, 14 of the drive shaft 7, as they are subjected to unavoidable wear-and-tear. For this purpose the drive shaft 7 must be de-mounted, which is effected by the following de-mounting measures:

The handpiece part 4 is to be separated from the motor part 2, which is effected by unscrewing the screw connection 28 between them.

The screw 17 is to be released by means of a spanner and to be removed with the roller 18.

Then, the internal casing 11 can be rearwardly withdrawn from the grip sleeve 4a.

In a further de-mounting step, the pressure piece 21 is to be rearwardly withdrawn from the internal casing 11, after previously or now unscrewing the front cap.

For de-mounting the roller bearing 14, a Quad-ring 29 and a disk 31 are further to be removed. Thereafter, the nut 16 is to be loosened with a spanner and unscrewed. In a next de-mounting step, the drive shaft 7 is to be urged rearwardly, completely out of the interior casing 11, for which purpose a suitably adapted tool is helpful. Hereby, a bush 32 which is arranged before the roller bearing 14 is also urged out by the drive shaft 7.

Then, the draw rod 10 supporting the plug-in connection section 23 can be rearwardly screwed out of the drive shaft 7.

After removal of a securing ring 33 by means of a pair of Seeger circlip tongs the rear roller bearing 13 can then be drawn off the bearing sleeve 7a with a draw-off device.

The forward roller bearing 14 can also be drawn off the inner casing 11 with a draw-off device.

Through this known configuration, great manufacturing outlay and in particular a great outlay in terms of mounting effort and time is inevitably involved in the exchange of the bearings 13, 14.

SUMMARY OF THE INVENTION

The object of the invention is to reduce the outlay involved in de-mounting the drive shaft, in particular for the exchange of its bearings, with a handpiece of the kind mentioned in the introduction.

With the handpiece according to the invention the drive shaft is forwardly or rearwardly de-mountable together with the bearings as a structural unit. Thereby, significant advantages are provided in particular with regard to the exchange of the drive shaft bearings, in particular simpler, gentler and quicker de-mounting and mounting, whereby advantages in manufacture are also achieved. Even non-specialists, e.g. a dental technician, can carry out an exchange without difficulty, whilst maintaining a high quality standard, whereby a reserve structural unit—made available to the user—can be used advantageously. This is the case not only for the structural unit but also for the roller bearings.

In the case of de-mounting forwardly, with the configuration according to the invention it is not necessary to separate the handpiece part from the motor part, which is in itself a significant simplification. The forward de-mounting of the drive shaft is in particular very advantageous because not only the forward bearing but also the rearward bearing is drawn out of the inner casing with the drive shaft. It is significantly simpler to draw the rearward bearing from the shaft in its de-mounted condition than to draw the rear bearing out of the inner casing separately, which although possible, can be carried out only with difficulty on account of the rearward position and may have to be carried out after rearward separation of the handpiece part from the motor part.

Also described herein are features which lead to further simplification with respect to manufacturing and installation, both with regard to the work effort required as well as with regard to time required. A further advantage of the invention lies in that the bearings can be mounted more gently and thus the danger of impairment or damage during mounting is reduced. Further features of the invention relate to improvement of sealing of the forward bearing, which is particularly greatly exposed to contamination.

BRIEF DESCRIPTION OF THE DRAWINGS

Below, the invention and further advantages achievable thereby are explained in more detail with reference to preferred exemplary embodiments and drawings, in which:

FIG. 1 shows a handpiece according to the invention in side view;

FIG. 2 shows the forward half of the handpiece in axial section;

FIG. 3 shows an internal casing of the handpiece in a view from above;

DETAILED DESCRIPTION OF PREFERRED EMBODIMENTS

Figure 4:
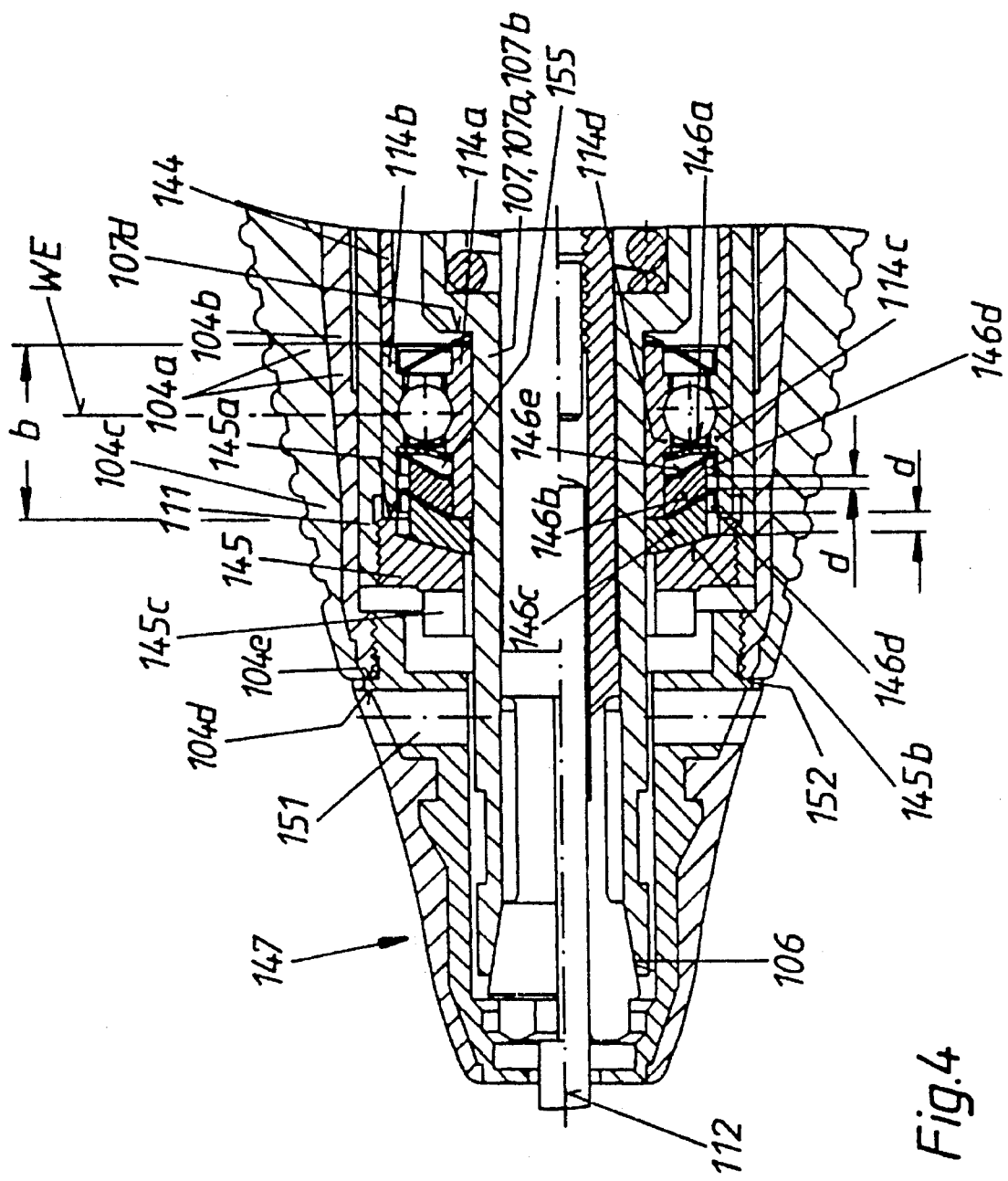
FIG. 4 shows a bearing seal, designated as X in FIG. 2, in longitudinal section to a larger scale.
Figure 5:
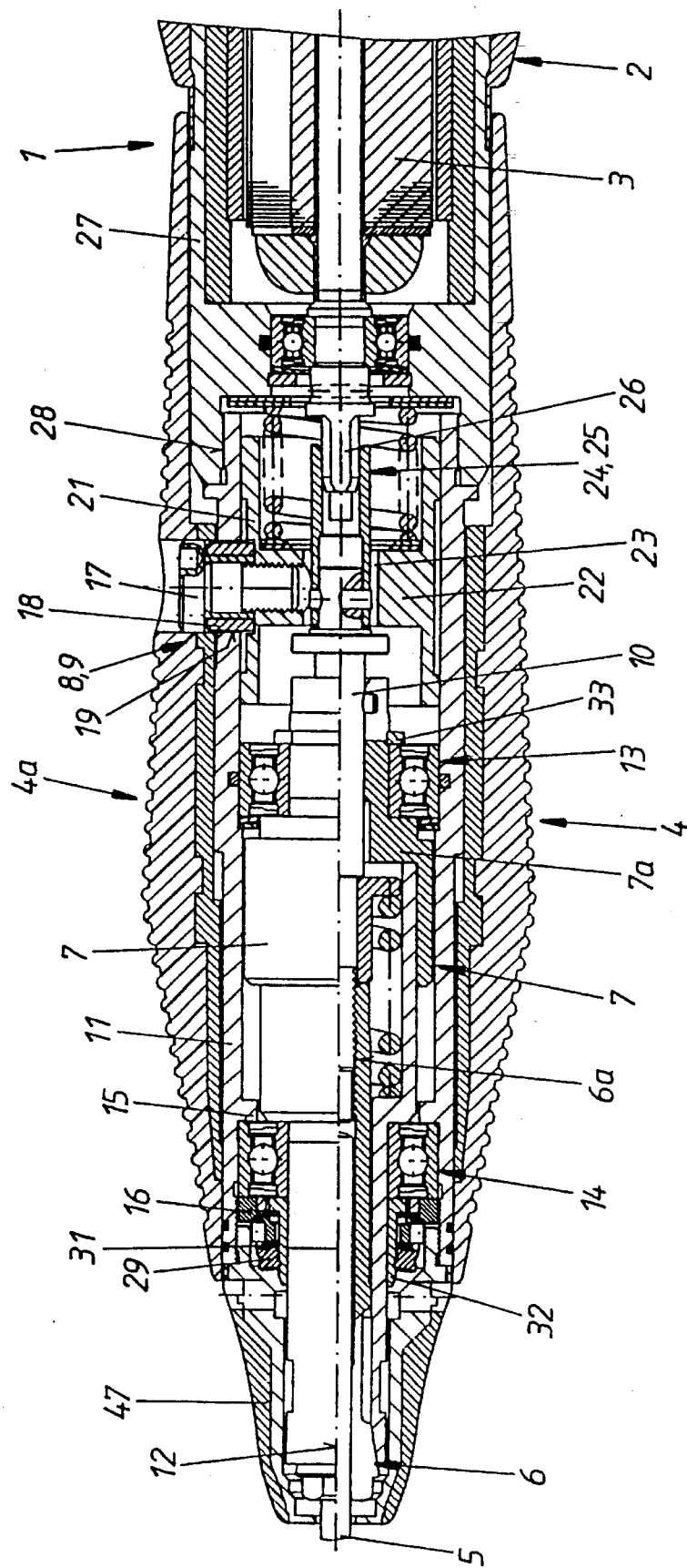
FIG. 5 shows the forward half of a prior art handpiece in an axial section.

The rod-like, straight handpiece 101 comprises a rearward motor part 102 with an in particular electric drive motor 103 mounted therein and a forward handpiece part 104 into which, from the front, a work tool can be mounted with its shaft 105. For this purpose there serves a sleeve-like, slotted clamping chuck 106 which is part of a drive shaft 107, which is rotatably mounted coaxially in the handpiece part 104 and is connected with the drive motor 103 for rotation. The clamping chuck 106 can be opened and closed by means of a relative rotation between the motor part 102 and a grip sleeve 104a of the handpiece part 104. For this purpose an actuating mechanism 108 is integrated into the handpiece part 104, which mechanism is effective between the grip sleeve 104a and the drive shaft 107 and has a transmission 109 which converts the rotary movement of the grip sleeve 104a into an axial movement of a round draw rod 110, which extends from the rear coaxially through a bearing sleeve 107a of the drive shaft 107, is mounted therein axially displaceably in a bore and is screwed into an internal thread 106a of the clamping chuck with its forward end. The grip sleeve 104a is mounted on a sleeve-like internal casing 111 to be rotatable around the longitudinal middle axis 112 of the handpiece 101 and to be longitudinally displaceable. In the internal casing 111, the drive shaft 107 is rotatably mounted by means of two roller bearings 113, 114 which have an axial spacing from one another. The motor part 102 can be connected by means of a cable 102a, and possibly a connection part 102b, to an energy supply source, in this case a current supply source; and/or a control apparatus.

The transmission 109 has a radial screw 117, which penetrates a radial hole in the grip sleeve 104a and, with a roller 118 penetrates a groove 119 in the internal casing 111 which runs obliquely in the circumferential direction, and is screwed into a pressure piece 121, which sits axially displaceably—with play for movement—in the rear end region of the hollow cylindrical internal casing 111 and has a central hole 123 in a middle inner ring 122, through which hole the drive shaft 107 projects with a plug-in connection section 124, which is connected with a drive pin 126 of the drive motor 103 by way of a plug-in coupling 125. FIG. 3 shows the internal casing 111 with the groove 119 in a view from above.

The motor part 102 also has an internal casing 127, in which the drive motor 103 is arranged and with which casing the motor part is screwed on to the rear end of the internal casing 111 of the handpiece part 104, at 128.

The grip sleeve 104a comprises a carrier sleeve 104b of metal and a sheathing 104c attached to the outer surface of the carrier sleeve, which sheathing may be made of grippable and/or soft elastic and/or heat isolating material, e.g. rubber or plastics, which can be either drawn over, formed on or sprayed on the outer surface. At the forward end, the sheathing 104c ends with the carrier sleeve 104b at a radial end surface 104d. The rear end of the sheathing 104c projects beyond the carrier sleeve 104b, this continuation preferably being mounted rotatably on the forward end region of the hollow cylindrical casing 127 of the motor part 2. Preferably, the casing 127 is also provided with a sheathing 127a which corresponds with the sheathing 104c.

The plug-in connection section 124 is preferably a sleeve 124a, which is mounted onto the rear end of the draw rod 110 and is fastened e.g. by means of a transverse pin, having a flange 124b at its forward end, which flange bears against a shoulder of the draw rod 110 which is rearwardly directed and with which an internal ring 122, arranged at spacing rearwardly thereof, cooperates.

Between the draw rod 110 and the bearing sleeve 107a there is a connection 135 such that they rotate together, which connection is formed by a transverse pin in the draw rod 110, the ends of which engage into a rearwardly open axial slit S in the rear end region of the bearing sleeve 107a.

The bearing sleeve 107a comprises a rear bearing sleeve part 107b and a forward bearing sleeve part 107c which are formed, at their mutually confronting end regions, in pot-like form, whereby they overlap in this region and are firmly connected with one another, e.g. are firmly pressed together. By this means an annular space 136 is provided which surrounds the rear end region of the clamping chuck 6 and the forward end of the draw rod 110, in which space a tensioning spring 137 in the form of a coiled compression spring is arranged, the forward end of which bears against an inner shoulder of the forward bearing sleeve part 107c and the rearward end of which presses rearwardly against a flange sleeve 138, which is seated fixedly on the draw rod 110 and in the present embodiment is screwed between the rearward end of the sleeve-like clamping chuck 106 and a shoulder 139 of the draw rod 110. At its forward end the bearing sleeve 107a has an internal conical surface 141a, which diverges forwardly, and against which an external conical surface 141b of the clamping chuck 106—which is known per se—is tensioned by means of the tensioning spring 137. In the tensioned position in accordance with FIG. 2 there is a spacing a between the flange sleeve 138 and the rear bearing sleeve part 107c, by means of which the tensioning is ensured on account of the force of the tensioning spring 137.

One of the two bearings 113, 114 is formed as a fixed bearing and the other as a loose bearing. In the present embodiment the rear roller bearing 113 is a fixed bearing. The inner ring thereof is arranged on a rearward bearing pin of the rear bearing sleeve part 107c and it is mounted between a rearwardly facing shoulder 107d and a screw ring 142 which is screwed onto the bearing pin. The outer ring of the roller bearing 113 bears against an internal shoulder 143 of the internal casing 111 with its rear end surface, a spacing sleeve 144 being arranged between the outer rings of the two roller bearings 113, 114, which is seated in the inner casing 111 with play for movement. The length of the spacing sleeve 144 is sufficiently great that there is a small spacing between the inner ring of the forward roller bearing 114 and a forwardly directed shoulder surface 107d of the forward bearing sleeve part 107b, whereby a ring spring may preferably be arranged between them. Thereby, the outer ring of the forward roller bearing 114 is screwed against the inner shoulder 143 through a screw ring 145 which is screwed into the forward end of the internal casing 111 by means of the spacing sleeve 144 and the outer ring of the roller bearing 113. Between the screw ring 145 and the forward roller bearing 114 there is a ring seal 146 for sealing off the roller bearing 114, which preferably at least partially forms a constructional unit with the roller bearing 114. Details of this ring seal 146 will be described below.

The grip sleeve 104a, which in the present embodiment forms an outer casing, is covered to the front by a front cap 147 with a middle through hole 148 for the tool or the shaft 105 thereof. Preferably the drive shaft 107 or the forward bearing sleeve part 107c project forwardly beyond the internal casing 111 and the grip sleeve 104a, and the front cap 147 has a dome-like cross-sectional form, so that a conical or truncated conical form results for the handpiece at the forward end thereof. Between the front cap 147 and the forward end region of the clamping chuck 106, and the drive shaft 107, there is a gap 149 which is necessarily present, which gap extends to the screw ring 145 or to the ring seal 146. In order to improve the cleaning effect of this gap through blowing out from the front, and at the same time to reduce the danger of dust penetrating the ring seal 146, at least one or several through holes, in the present embodiment two mutually opposing through holes 151 which radially extend from the gap 149, are provided in the front cap 147, through which the compressed air and the dust can escape upon blowing out.

The front cap 147 is screwed together with the carrier sleeve 104b. Preferably, for this purpose there is provided at the rear end of the front cap 147 an attachment 153—preferably of annular form and having an external thread—extending rearwardly from a radial annular shoulder 152, with which attachment the front cap 147 is screwed into a corresponding internal thread 104d at the forward end of the carrier sleeve 104b, the annular shoulder 152 being screwed against the forward end surface 104e of the carrier sleeve 104b, whereby a screw stop is formed. Preferably the front cap 147 is also provided with a sheathing 147a which corresponds to the sheathing 104c. As is the case with the sheathing 104c, there are provided form-fitting connections 154 also between the front cap 147 and the sheathing 147a, which are formed by protrusions and/or recesses, for securing the sheathing concerned on to its supporting body.

The ring seal 146 comprises at least two, preferably three sealing disks 146a, 146b, 146c which are preferably assembled together in the manner of a seal pack or bear against each other longitudinally of the middle axis 112 and are in particular integrated into the forward roller bearing 114 externally or on the forward side. The width b of the roller bearing 114 is larger than the conventional standardized width of this type, whereby the outer and inner ring are both equally forwardly extended, so that the roller bodies, in this case balls, or the roller bearing plane WE, is or are arranged eccentrically, i.e. rearwardly offset, off-center. By this means a free annular space 155 is provided between the outer ring and the inner ring to the forward side of the roller bodies, in which space at least the first two sealing disks 146a, 146b and possibly also the third sealing disk 146c are arranged. In the present embodiment the first two sealing disks 146a, 146b are seated in the annular space 155, and the third, i.e. the foremost sealing disk 146c is seated with its outer circumferential region either entirely or partly in the annular space 155 and with its inner circumferential region outside the annular space 155, whereby it engages over the sleeve-like section of the bearing sleeve part 107c supporting the inner ring of the roller bearing 114 and preferably bears against the forward end surface of the inner ring 114a.

In the present embodiment the sealing disks 146a, 146b, 146c are held on the outer ring 114b, and are—in particular bearing axially against one another—urged against a shoulder 114c of the outer ring, preferably through the screw ring 145, which presses laterally from the front against the respective foremost sealing disk, in the present case disk 146c.

The first or the rearmost sealing disk 146a is a thin, preferably flat disk of elastically flexible materials in particular of plastics, preferably Teflon. The thickness of the disk is a few tenths of a millimeter, preferably approx. 0.15 mm. It bears against the internal shoulder 114c with its outer edge region, being of such a size that it can be pushed into the outer ring 114b with little play for movement. Radially opposite, a shoulder 114d is arranged on the inner ring 114a, against which the first sealing disk 146a bears with its inner edge region. The shoulder 114d is slightly offset axially forwardly with regard to the shoulder 114c, preferably by approximately 0.05 mm. On account of this offset, the first sealing disk 146a, which in the present embodiment is planar, is—in the installed position—flexed axially outwardly on the inside, whereby it bears against the shoulder 114d with a slight axial, rearwardly directed elastic force. By this means an excellent sealing off of the roller bodies is provided, which ensures reliable sealing even in the presence of manufacturing tolerances which are hardly to be avoided, because the first sealing disk 146a always bears glidingly against the sealing surface, namely the shoulder 114d, due to its outwardly flexed and elastically biassed position and the thereby predetermined spring deformation. The inner diameter of the first sealing disk 146a may be of such a size that its inner surface has a small radial spacing from the cylindrical surface of the inner ring 114a or the inner surface of the first sealing disk 146a can also exercise a sealing function with the cylindrical surface of the inner ring 114a, if there is only little play for movement between them.

Particularly good sealing results are achieved if the first sealing disk 146a consists of a fibre or textile reinforced plastics, in particular teflon.

The second and preferably also the third sealing disk 146b, 146c are each preferably a felt ring or a felt disk, both or only the second of which glide sealingly on the inner ring 114a, whereby the third sealing disk 146c can glide on the forward bearing sleeve 107c as has been described above. Preferably, respective stabilizing rings 146d are associated with the second and the third sealing disks 146b, 146c, against which the associated sealing disk can bear axially or can also be attached thereto, e.g. through gluing. The stabilizing rings 146d, which are similar to one another, each comprise a hollow cylindrical supporting ring from which— in particular at the rearward end thereof—an inner flange 146e extends radially inwardly, which is preferably formed as a hollow cone, whereby its cone surface converges in particular forwardly. The associated sealing disk bears against this plate-spring-like form, preferably on the forward side of the inner flange 146e. The axial width of the supporting rings or the axial thickness of the second or third sealing disk 146b, 146c is in each case such that a spacing d is present between the supporting rings and between the foremost supporting ring and the screw ring 145 in the installed position. By this means, an axial pressure can be exerted upon the second or the third sealing ring 146b, 146c by the screw ring 145. Preferably the arrangement is such that a predetermined axial pressure is achieved when the screw ring 145 bears against a screw stop 145a, which in the present embodiment is formed by the forward end of the outer ring 114b.

In the present embodiment a small radial spacing is provided between the outer circumference of the sealing disks 146b, 146c and the outer ring 114b, into which the supporting ring of the associated stabilizing ring 146d projects.

The internal dimension of the screw ring 145 is preferably only slightly greater than the size of the bearing sleeve 107c projecting through it, so that the screw ring 145 can, with its rearwardly directed pressure surface 145b, support the sealing disk 146c which bears against it over as large an area as possible and can support it in particular on its inner edge. Preferably the pressure surface 145b is a hollow cone surface, which converges forwardly.

The stabilizing rings 146d may be per se known cover rings of either metal or plastics. Such a cover ring is also arranged on the rear side of the roller bearing 114.

The de-mounting of the drive shaft 107 and the roller bearings 113, 114 and the ring sealing 146, or an exchange thereof, is effected by means of the following de-mounting steps. After screwing off the screw 117 and the front cap 147, only the screw ring 145 needs to be screwed off by means of a tool which engages into forward side engagement openings 145c. Inasfar as the third sealing disk 146c is loosely mounted on the stabilizing ring 146d, it may be removed. Then, the complete drive shaft 107 can be forwardly pulled out of the internal casing 111 together with the roller bearings 113, 114 and the spacing sleeves 144 arranged therebetween, which may be effected manually since the inner rings of the roller bearings 113, 114 are seated in the internal casing 111 with a comparatively easily moveable fit. The rearward roller bearing 113 is necessarily de-mounted together with the drive shaft 107, since it is attached to the latter. In the de-mounted condition, the screw ring 142 can be readily screwed off the drive shaft 107. Then, the roller bearing 113 and, if appropriate, now the roller bearing 114 with the ring seal 146, may be readily drawn off of the drive shaft 107, preferably by means of associated draw-off devices.

This embodiment makes it possible for the user to exchange the roller bearings 113, 114 and/or the ring seal 146 in a simple and rapid manner. It is advantageous for the user to keep one set of roller bearings and if appropriate also a ring seal 146 in store, so that the handpiece can be remounted and used again within a short time, at the place of use. Dispatch of the roller bearing to the manufacturer, as is the case with the known configuration, is not necessary.

Mounting or installation is effected with a reversed order of steps. Firstly, the roller bearings 113, 114 are pushed onto the drive shaft 107 and the rearward roller bearing 113 is secured by the screw ring 142. In the event that the ring seal 146 at least partially forms a constructional unit with the forward roller bearing 114, the ring seal 146 is simultaneously mounted. Then, the thus pre-assembled drive shaft unit is inserted into the internal casing 111 from the front and is positioned and secured through the screwing in of the screw ring 145, whereby—firstly—the third sealing disk 146c may be additionally mounted as a separate individual part. Thereafter, merely screwing in of the front cap 147 and the screw 117 is required.

With the de-mounting and mounting or installation procedures, the plug-in coupling 124 allows de-mounting and also mounting or installation in a simple manner.

I claim:

1. A straight handpiece (101) for medical and dental purposes; comprising a sleeve-like casing (111); a clamping device (106) arranged in said casing for the selective clamping of tools (105) insertable into the handpiece (101) from a front end thereof; a drive shaft (107) which is rotatably mounted in the casing (111); a rearward and a forward roller bearing (113, 114) supporting said clamping device (106) on said drive shaft; a first shoulder (143) on the casing (111) against which there bears an outer ring of one of the roller bearings (113) for axially retaining the drive shaft; a releasable arresting shoulder (145) being positioned opposite to the first shoulder (143) at an axial spacing therewith, the first shoulder (143) being arranged on the outside of the outer ring of the rearward roller bearing (113), the arresting shoulder (145) being arranged on the outside of the forward roller bearing (114), the drive shaft (107) being demountable and mountable as a modular unit with the roller bearings (113, 114) from the side of the casing (111) on which the releasable arresting shoulder (145) is located, the outer ring of the forward roller bearing (114) being rearwardly located in contact with an internal shoulder of the casing (111); a ring seal (146) being arranged between the internal shoulder and the forward roller bearing (114), and wherein the first shoulder (143) is arranged at the rear side of the rearward roller bearing (113) and the modular unit is demountable to the front and remountable from the front of the handpiece.

2. A motorized handpiece according to claim 1, wherein screw means (145) which is engaged in the casing (111) screws the outer ring of the forward roller bearing (114) against the internal shoulder of the casing (111), said ring seal (146) being arranged between said screw means and the forward roller bearing (114) and said screw means presses against said seal ring (146).

3. A motorized handpiece according to claim 1, wherein the first shoulder is arranged at the forward side of the forward roller bearing (114) and the modular unit is demountable to the rear and remountable from the rear of the handpiece.

4. A motorized handpiece according to claim 1, wherein the rearward roller bearing (113) comprises a fixed bearing and the forward roller bearing (114) comprises a loose-running bearing.

5. A motorized handpiece according to claim 1, wherein a spacing sleeve (144) is arranged between the outer rings of each of the roller bearings (113, 114).

6. A motorized handpiece according to claim 1, wherein the forward roller bearing (114) has the ring seal (146) located at the forward side of roller bodies of the bearing, said ring seal being arranged to be operative between inner and outer rings (114a, 114b), the roller bearing (114) being wider towards the front thereof relative to the roller bodies.

7. A motorized handpiece according to claim 1, wherein the forward roller bearing (114) and at least a part of the ring seal (146) constitute a modular structural unit.

8. A motorized handpiece according to claim 1, wherein an actuating part of the handpiece comprises a grip sleeve (104a) surrounding the casing (111), said sleeve projecting forwardly beyond the casing (111), and the handpiece includes dome-like front cap (147) at a forward end, said cap being screwed to the grip sleeve (104a) in the projecting region of the sleeve.

9. A motorized handpiece according to claim 8, wherein the grip sleeve (104a) is selectively coated on its outer surface with a soft elastic and heat insulating material.

10. A motorized handpiece according to claim 1, wherein the drive shaft (107) comprises a round sleeve (107a) which in the forward end region thereof includes an internal cone diverging forwardly; and a slotted clamping sleeve (106) being coaxially mounted in said cone so as to be longitudinally displaceable, said clamping sleeve having in the forward end region thereof an external cone which cooperates with the internal cone.

11. A motorized handpiece according to claim 10, wherein the clamping sleeve (106) is connected with a draw rod (110) rearwardly penetrating the sleeve (107a), said rod being connected in the rearward end region thereof with the actuating part (104a) by a transverse pin (117), the actuating part (104a) being mounted so as to be rotatable in a circumferential direction and the transverse pin (117) penetrating a groove (119) in the casing (111) which extends obliquely in the circumferential direction.

12. A motorized handpiece according to claim 1, wherein the rearward roller bearing (113) bears against a rearwardly directed shoulder of the drive shaft (107) and is bounded at the rearward side thereof by a securing ring.

* * * * *